United States Patent
Hauth et al.

[11] 4,004,011
[45] Jan. 18, 1977

[54] 3-PYRIDYLAMINE SUBSTITUTED ERGOLINES

[75] Inventors: Hartmut Hauth, Riehen; Hans Tscherter, Neuallschwil, both of Switzerland

[73] Assignee: Sandoz Ltd., Basel, Switzerland

[22] Filed: Apr. 9, 1975

[21] Appl. No.: 566,355

[30] Foreign Application Priority Data

Apr. 16, 1974 Switzerland ............. 5234/74
Feb. 14, 1975 Switzerland ............. 1893/75
Feb. 14, 1975 Switzerland ............. 1894/75

[52] U.S. Cl. ............. 424/261; 260/285.5
[51] Int. Cl.[2] ............. C07D 457/12
[58] Field of Search ............. 260/285.5; 424/261

[56] References Cited
OTHER PUBLICATIONS

Stoll et al; Helo. Chem. Acta. vol. 35, pp. 1249–1258 (1951).

*Primary Examiner*—Donald G. Daus
*Assistant Examiner*—Mary C. Vaughn
*Attorney, Agent, or Firm*—Gerald D. Sharkin; Robert S. Honor; Thomas O. McGovern

[57] ABSTRACT

This invention provides new compounds of formula I,

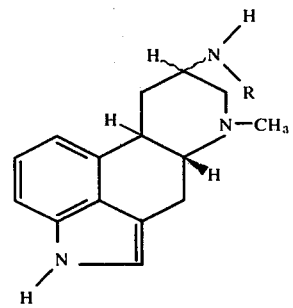

wherein R is 3-pyridyl or 3-pyridyl mono- or polysubstituted
by lower alkyl, lower alkoxy, lower alkylthio, phenoxy, halogen, hydroxy, or the group

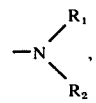

wherein each of $R_1$ and $R_2$ is, independently, hydrogen or lower alkyl,
useful as prolactin secretion inhibitors for the treatment of galactorrhea.

40 Claims, No Drawings

3-PYRIDYLAMINE SUBSTITUTED ERGOLINES

The present invention relates to new heterocyclic compounds.

In accordance with the invention there are provided new compounds of formula I,

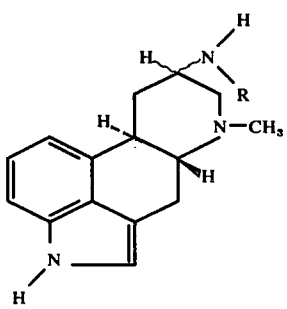

wherein

R is 3-pyridyl or 3-pyridyl mono- or polysubstituted by lower alkyl, lower alkoxy, lower alkylthio, phenoxy, halogen, hydroxy, or the group

wherein each of $R_1$ and $R_2$ is, independently, hydrogen or lower alkyl.

Further, in accordance with the invention a compound of formula I may be obtained by a process comprising reducing the compound of formula II

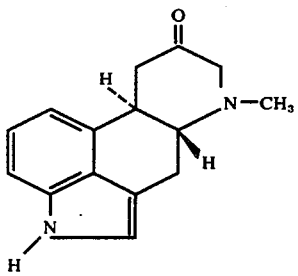

physically or chemically associated with an amine of formula III,

    III wherein R is as defined above.

It will be appreciated that a compound of formula Ia,

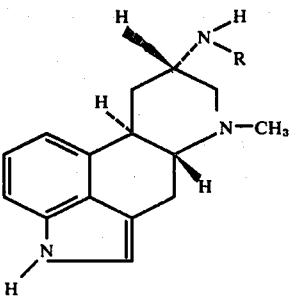

or of formula Ib,

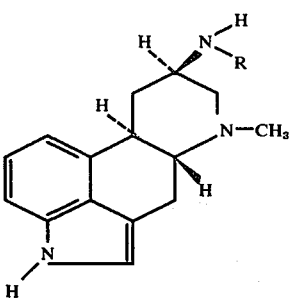

wherein R is as defined above, may be separated or purified in conventional manner.

Halogen is preferably fluorine, bromine, especially chlorine.

The alkyl, alkoxy and alkylthio groups indicated as substituents of the pyridine ring, as well as the alkyl groups represented by the symbols $R_1$ and $R_2$, preferably contain 1 to 4 carbon atoms.

Preferably polysubstituted means di- or especially monosubstituted.

Preferably any substituent is ortho to the pyridyl nitrogen ring atom, especially para to the aminoergoline substituent.

When the compound of formula II is physically associated with a compound of formula III, the reduction in accordance with the invention is conveniently effected by catalytic hydrogenation in the presence of a noble metal catalyst, preferably palladium metal, which may optionally be used on carriers, e.g. active charcoal. Hydrogenation is preferably effected in a suitable organic solvent, e.g. a lower aliphatic alcohol e.g. methanol, or carboxylic acid, e.g. glacial acetic acid. Hydrogenation may be effected at room pressure.

When the compound of formula II is chemically associated with a compound of formula III, the resultant association may be in the form of a Schiff's base. The reduction is preferably effected in conventional manner for the reduction of Schiff bases, e.g. with a reducing agent such as sodium borohydride or cyanoborohydride. A suitable temperature is around 0° C.

The reaction is preferably effected in an inert organic solvent such as a mixture of methanol or dioxane.

Schiff bases may be prepared in conventional manner, e.g. by fusing a compound of formula II and a compound of formula III in an inert atmosphere preferably in the presence of a suitable condensation agent, e.g. potassium carbonate. If desired the Schiff bases may be used in-situ.

The purification of the resulting reaction mixture may be effected in accordance with known methods, e.g. by chromatography on e.g. silica gel with a suitable solvent mixture, such as a chlorinated hydrocarbon (e.g. methylene chloride)/lower aliphatic alcohol (e.g. methanol) with varying ratios.

The compound of formula II may for example be obtained by reacting a compound of formula V,

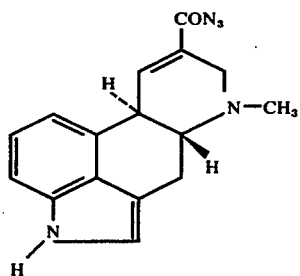

with an acid.

A suitable acid is a mineral acid such as aqueous hydrochloric acid. The reaction is preferably effected at an elevated temperature, e.g. under reflux.

The compound of formula V may be obtained by reacting a reactive functional derivative of 6-methyl-$\Delta^{8,9}$-ergolene-8-carboxylic acid of formula IV

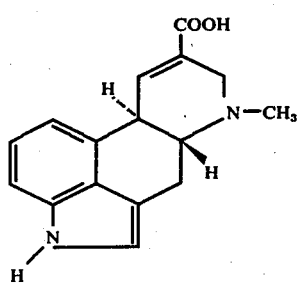

with an alkali azide in an inert dry solvent.

An example of a reactive functional derivative of 6-methyl-$\Delta^{8,9}$-ergolene-8-carboxylic acid, which may be used, is the addition product with a complex formed from an N-di(lower)alkyl-substituted acid amide of an aliphatic monocarboxylic acid containing 1 to 3 carbon atoms, preferably dimethyl formamide, and a halogenating agent such as oxalyl chloride, phosgene or thionyl chloride.

The acid chloride hydrochloride, the addition product with carbodiimide or mixed anhydrides of the acid of formula IV with sulphuric acid or trifluoroacetic acid, which may be produced in known manner, may alternatively be used.

Suitable reaction temperatures are from −20° to 20° C. A suitable azide is sodium azide.

Acid addition salt forms of compounds of formula I may be obtained in conventional manner from free base forms and vice versa. A suitable acid for salt formation is tartaric acid, maleic acid, hydrochloric acid or hydrobromic acid. The compounds may exist in solvated crystalline form, e.g. in hydrate form.

Insofar as the production of any starting material is not particularly described, these compounds are known or may be produced and purified in accordance with known processes, or in a manner analogous to processes described herein or to known processes.

In the following non-limiting Examples all temperatures are indicated in degrees Centigrade.

It will be appreciated that in some instances 3-pyridyl when substituted is preferably referred to as 5-pyridyl.

EXAMPLE 1

6-methyl-8-(3-pyridyl)amino-ergoline 24.0 g of 6-methyl-8-oxo-ergoline, 34.0 g of 3-aminopyridine and 4.0 g of potassium carbonate are heated to 150° in a sulphonating flask in an atmosphere of nitrogen and are kept at this temperature for 6 hours. After this reaction time, the Schiff's base obtained in the form of a black mash is dissolved in 400 cc of methanol/dioxane (1 : 1), the solution is cooled to 0° and reduced by the portionwise addition of 18.9 g of sodium borohydride at 0° within one hour while stirring. The reaction mixture is evaporated to dryness in a rotary evaporator, is taken up in 2.5 liters of methylene chloride and washed six times with one liter of water. The water phases are successively shaken with one liter of methylene chloride. The combined organic phases are dried over sodium sulphate, treated with 3 g of active charcoal, filtered through talc and concentrated by evaporation. The residue obtained in the form of a brown foam is purified by dissolving in 500 cc of ethanol, and is precipitated as tartrate by the addition of a solution of 22.5 g of L(+)-tartaric acid in one liter of ethanol. The tartrate is filtered off, washed with 200 cc of ether and dried. The resulting salt is dissolved in 1.5 liters of water whilst hot, the pH of this solution is adjusted to 7 with 2 N potassium hydroxide and the solution is extracted thrice with 2 liter amounts of methylene chloride. The methylene chloride phases are dried over sodium sulphate, filtered through talc and concentrated by evaporation. The resulting crude base is chromatographed on 800 g of silica gel (Merck 0.05 − 0.2 mm) with methylene chloride/methanol (98 : 2). The pure base is obtained in the form of a foam. This base is dissolved in 20 cc of methanol, and 3 cc of distilled water are added, whereby 6-methyl-8-(3-pyridyl amino-ergoline (8R/8S mixture) crystallizes. M.P. 125° − 131°;

$[\alpha]_D^{20} = +70.1°$ (c = 0.998, pyridine)

$[\alpha]_D^{20} = +100.4°$ (c = 0.954, chloroform).

Bis-[6-methyl-8-(3-pyridyl-amino)ergoline]tritartrate

A warm solution of 10.2 g of L(+)tartaric acid in 300 cc of ethanol is added to 14.5 g of 6-methyl-8-(3-pyridyl-amino)ergoline dissolved in 300 cc of ethanol. The tritartrate precipitates immediately. The mixture is kept at 0° for one hour and is filtered. The crystals are washed with 30 cc of ethanol and are subsequently dried in a high vacuum at 80°. In this manner bis-[6-methyl-8-(3-pyridyl-amino)ergoline]tritartrate, having a M.P. of 151° − 153°, is obtained;

$[\alpha]_D^{20} = -57.9°$ (c = 0.342, ethanol).

EXAMPLE 2

6-methyl-8-(3-pyridylamino)ergoline 17.8 g of 6-methyl-8-oxo-ergoline hydrogen maleate and 23.5 g of 3-aminopyridine in 500 cc of methanol are hydrogenated with the addition of 12 g of 10% palladium on active charcoal under normal conditions. After the hydrogen take up is complete (approx. 120 hours), the catalyst is filtered off, the filtrate is concentrated in a vacuum at a water bath temperature of 60°, and the resulting residue is purified and separated by chromatography on a 30-fold quantity of silica gel with methylene chloride and the addition of increasing amounts of methanol.

Chromatographic separation into the isomers is effected as follows:

Elution with methylene chloride with the addition of 2% or 3% of methanol yields the isomer I*a*

6-methyl-8S-(3-pyridylamino)ergoline,

M.P. 160°–161° (from acetone);

$[\alpha]_D^{20} = +70° \pm 3°$ (c = 0.58, pyridine) or = $+41° \pm 2°$ (c = 0.56, methanol).

The dihydrochloride crystallizes from isopropanol/ether with a M.P. from 220° (decomp.-/vacuum);

$[\alpha]_D^{20} = -38°$ (c = 0.48, 50% ethanol).

Further elution with methylene chloride with the addition of 3% to 5% of methanol yields mixtures and then the pure isomer I*b*

6-methyl-8R-(3-pyridylamino)ergoline

M.P. 230° – 232° (from acetone);

$[\alpha]_D^{20} = -82° \pm 3°$ (c = 0.52, pyridine) or = $-40° \pm 2°$ (c = 0.52, methanol).

EXAMPLE 3

6-methyl-8-(2-methoxy-5-pyridylamino)ergoline

A solution of 35.6 g of 6-methyl-8-oxo-ergoline in 1.4 liters of glacial acetic acid is slowly added dropwise to 35 g of 10% palladium on active charcoal and 18.6 g of 2-methoxy-5-aminopyridine in 400 cc of glacial acetic acid with simultaneous hydrogenation under normal conditions. The addition is effected within about 7 hours. After the hydrogen take up is complete, the catalyst is filtered off, the filtrate is concentrated in a vacuum and the resulting residue is taken up in methylene chloride (+15% of isopropanol) and washed with ice-cooled ammonia and water. The residue obtained after drying the combined organic phases and concentrating by evaporation, is purified and separated into the isomers by chromatography on an 80-fold quantity of silica gel with methylene chloride and the addition of increasing amounts of methanol.

Elution with methylene chloride with the addition of 2% of methanol yields the isomer I*a*

6-methyl-8S-(2-methoxy-5-pyridylamino)ergoline

Dihydrochloride: M.P. from 225° decomp. (from methanol/acetone);

$[\alpha]_D^{20} = -78° \pm 3°$ (c = 0.5 in ethanol/water 1:1).

Further elution with methylene chloride with the addition of 4% of methanol yields the isomer I*b*

6-methyl-8R-(2-methoxy-5-pyridylamino)ergoline

M.P. from 265° decomp. (from methanol/acetone)

$[\alpha]_D^{20} = -78° \pm 3°$ (c = 0.5 in pyridine).

Dihydrochloride: M.P. from 200° decomp. (from isopropanol)

$[\alpha]_D^{20} = -38° \pm 3°$ (c = 0.5 in ethanol/water 1 : 1).

EXAMPLE 4

6-methyl-8-(2-ethoxy-5-pyridylamino)ergoline

The following compounds (isomers I*a* and I*b*) are obtained in a manner analogous to that described in Example 3, from 2-ethoxy-5-aminopyridine and 6-methyl-8-oxo-ergoline in the presence of palladium:

6-methyl-8S-(2-ethoxy-5-pyridylamino)ergoline

M.P. 148° – 150° (from acetone/ether)

$[\alpha]_D^{20} = +68° \pm 3°$ (c = 0.5 in pyridine)

6-methyl-8R-(2-ethoxy-5-pyridylamino)ergoline

M.P. from 270° decomp. (from methanol/ether)

$[\alpha]_D^{20} = -70° \pm 3°$ (c = 0.5 in pyridine).

EXAMPLE 5

6-methyl-8-(2-isopropoxy-5-pyridylamino)ergoline

The following compounds (isomers I*a* and I*b*) are obtained in a manner analogous to that described in Example 3, from 2-isopropoxy-5-aminopyridine and 6-methyl-8-oxo-ergoline in the presence of palladium:

6-methyl-8S-(2-isopropoxy-5-pyridylamino)ergoline

M.P. 104°–105° (from acetone/ether)

$[\alpha]_D^{20} = +65° \pm 3°$ (c = 0.5 in pyridine)

6-methyl-8R-(2-isopropoxy-5-pyridylamino)ergoline

M.P. 243°–244° (from acetone/ether)

$[\alpha]_D^{20} = -77° \pm 3°$ (c = 0.5 in pyridine).

EXAMPLE 6

6-methyl-8-(2-n-butoxy-5-pyridylamino)ergoline

The following compounds (isomers I*a* and I*b*) are obtained in a manner analogous to that described in Example 3, from 2-n-butoxy-5-aminopyridine and 6-methyl-8-oxo-ergoline in the presence of palladium:

6-methyl-8S-(2-n-butoxy-5-pyridylamino)ergoline

M.P. 81°–82° (from ether/petroleum ether)

$[\alpha]_D^{20} = +67° \pm 3°$ (c = 0.5 in pyridine)

Dihydrobromide: M.P. from 205° decomp.

$[\alpha]_D^{20} = -37° \pm 3°$ (c = 0.5 in ethanol/water 1:1)

6-methyl-8R-(2-n-butoxy-5-pyridylamino)ergoline

M.P. 185°–187° (from methanol/ether)

$[\alpha]_D^{20} = -67° \pm 3°$ (c = 0.5 in pyridine)

Dihydrobromide: M.P. from 225° decomp. (from methanol/ether);

$[\alpha]_D^{20} = -35° \pm 3°$ (c = 0.5 in ethanol/water 1:1).

EXAMPLE 7

6-methyl-8-(2-tert.butoxy-5-pyridylamino)ergoline

The following compounds (isomers I$a$ and I$b$) are obtained in a manner analogous to that described in Example 3, from 2-tert.butoxy-5-aminopyridine and 6-methyl-8-oxo-ergoline in the presence of palladium:

6-methyl-8S-(2-tert.butoxy-5-pyridylamino)ergoline

Hydrogen maleate hydrate: M.P. 112°–114° (from acetone/ether;

$[\alpha]_D^{20} = -35° \pm 3°$ (c = 0.5 in ethanol/water 1:1)

6-methyl-8R-(2-tert.butoxy-5-pyridylamino)ergoline

M.P. 244°–246° (from methanol/ether)

$[\alpha]_D^{20} = -78° \pm 3°$ (c = 0.5 in pyridine).

EXAMPLE 8

6-methyl-8-(2-phenoxy-5-pyridylamino)ergoline

The following compounds (isomers I$a$ and I$b$) are obtained in a manner analogous to that described in Example 3, from 2-phenoxy-5-aminopyridine and 6-methyl-8-oxo-ergoline in the presence of palladium:

6-methyl-8S-(2-phenoxy-5-pyridylamino)ergoline

M.P. 186°–188° (from acetone/ethyl acetate)

$[\alpha]_D^{20} = +64° \pm 3°$ (c = 0.5 in pyridine)

6-methyl-8R-(2-phenoxy-5-pyridylamino)ergoline

M.P. 240°–241° (from methanol/acetone)

$[\alpha]_D^{20} = -70° \pm 3°$ (c = 0.5 in pyridine).

The following compounds, which may likewise be separated into their isomers, may also be produced in a manner analogous to that described in Examples 2 to 8, using the corresponding amines:

| Example | Compound |
|---|---|
| 9 | 6-methyl-8-(2-methyl-5-pyridylamino)ergoline |
| 10 | 6-methyl-8-(2-hydroxy-5-pyridylamino)ergoline |
| 11 | 6-methyl-8-(2-chloro-5-pyridylamino)ergoline |
| 12 | 6-methyl-8-(2,6-dimethoxy-3-pyridylamino)-ergoline |
| 13 | 6-methyl-8-(2-dimethylamino-5-pyridylamino)-ergoline |
| 13 a | 6-methyl-8-(2-amino-5-pyridylamino)-ergoline. |

EXAMPLE 14

6-methyl-8-(2-thiomethyl-5-pyridylamino)ergoline

The following compound may be obtained in a manner analogous to that described in Example 1, from 2-thiomethyl-5-aminopyridine and 6-methyl-8-oxo-ergoline in the presence of sodium borohydride:

6-methyl-8S-(2-thiomethyl-5-pyridylamino)ergoline

Tartrate hemihydrate: M.P. decomp. from 218° (from methanol/acetone);

$[\alpha]_D^{20} = +70° \pm 5°$ (c = 0.1 in pyridine).

The 6-methyl-8-oxo-ergoline, used as starting material, may for example, be obtained as follows:

a. 6-methyl-$\Delta^{8,9}$-ergolene-8-carboxylic acid azide hydrochloride 23 cc of absolute dimethyl formamide are added to 100 cc of absolute chloroform in a sulphonating flask in an atmosphere of nitrogen, and the mixture is cooled to −20°. A solution of 10.4 cc of oxalyl chloride in 50 cc of absolute chloroform is allowed to flow into the mixture within 15 to 20 minutes while stirring, and stirring is continued for about 20 minutes.

77 cc of absolute dimethyl formamide are added to 26.8 g of 6-methyl-$\Delta^{8,9}$-ergolene-8-carboxylic acid suspended in 200 cc of absolute chloroform in an atmosphere of nitrogen, and the mixture is cooled to −30°. The solution prepared as described above is then added in an atmosphere of nitrogen, whereby the temperature rises slightly and the initial gray-brown colour turns violet.

The resulting reaction mixture is added at −20° to a suspension of 14.3 g of pulverized sodium azide in 300 cc of absolute chloroform in an atmosphere of nitrogen while stirring vigorously, and is rinsed again with a small amount of chloroform. The reaction mixture is further stirred for one hour without cooling bath, whereby the temperature rises to about +15° and the reaction mixture turns green-black coloured. Centrifuging is subsequently effected for 20 minutes in a centrifuge at 3000 r.p.m. The green-black solution is decanted, the resulting residue is again taken up in 300 cc of chloroform and filtered off on a glass sinter suction filter (G 3). The filter residue is suspended thrice with 200 cc of amounts of ice water, is sucked off each time and finally washed with 300 cc of diethyl ether. 6-methyl-$\Delta^{8,9}$-ergolene-8-carboxylic acid azide hydrochloride is obtained as dark green product which is used for the next reaction step without drying.

b. 6-methyl-8-oxo-ergoline 1000 cc of boiling 0.2 N hydrochloric acid are poured over the undried, crude 6-methyl-$\Delta^{8,9}$-ergolene-8-carboxylic acid azide hydrochloride obtained in step (a) above, whereby a strong nitrogen evolution occurs immediately. Heating is continued in a preheated oil bath of 150°–160° until nitrogen evolution is complete and the black-brown suspension turns clear. Cooling is then effected to room temperature, the mixture is covered with a layer of 2000 cc of diethyl ether, and is rendered alkaline (pH 8) with about 150 cc of 1 N sodium hydrogen carbonate while stirring.

The layers are separated by again extracting the aqueous phase three times with 500 cc amounts of diethyl ether and washing the ether phases twice with 200 cc amounts of water. The ether extracts are dried over sodium sulphate, 2 g of active charcoal are added, stirring is effected for 3 minutes and filtration is effected through a layer of Hyflo until clear. The filtrate is concentrated to about 50 cc in a vacuum, whereby 6-methyl-8-oxo-ergoline crystallizes as yellow or light brown compound. M.P. 206° (decomp.) or in a high vacuum 228° (decomp.);

$[\alpha]_D^{20} = -78°$ (c = 0.5, pyridine).

The compounds of formula I have not been described in the literature.

The compounds of formula I are useful because the possess pharmacological activity in animals. In particular, the compounds of formula I are useful as prolactin secretion inhibitor agents, useful for example in the treatment of galactorrhea, as indicated by an inhibition of physiologically stimulated prolactin secretion, when after isolation a lactating rat is brought into contact again with other lactating rats in accordance with the principles of Grosvenor and Mena, J. Endocr. 52, 11 (1972), on s.c. administration of from about 5 to about 15 mg/kg animal body weight of the compounds and additionally by an inhibition of tonic prolactin secretion in male rats by means of prolactin level determinations in the rat sera by radioimmunoassay on s.c. administration of from about 0.005 to about 1.0 mg/kg animal body weight of the compounds, and further by an inhibition of DMBA-induced mamma tumours in rats, on s.c. administration of from about 5 to about 15 mg/kg animal body weight of the compounds.

Additionally the compounds are useful as anti-Parkinson agents for the treatment of M. Parkinson, as indicated by central dopaminergic stimulant activity as indicated by for example standard tests, e.g. by an antagonism of tetrabenazine-induced catalepsy in rats on i.p. administration of from about 5 to about 50 mg/kg animal body weight of the compounds and by an induction of turning movements in rats which have been lesioned with injections of 6-hydroxy-dopamine in the nigrostriatal pathways, on s.c. administration of from about 0.5 to about 50 mg/kg animal body weight of the compounds.

For the above mentioned uses the dosage will, of course, vary depending on the compound employed, mode of administration and therapy desired. However, in general, satisfactory results are obtained when administered at a daily dosage of from 0.005 mg to about 50 mg per kg animal body weight, conveniently given in divided doses 2 to 4 times a day or in sustained release form. For the larger mammal, the daily dosage is in the range from about 0.005 to about 1 mg per kg animal body weight, i.e. a total daily dosage of from about 0.5 to about 50 mg, and dosage forms suitable for oral administration comprise from about 0.1 mg to about 25 mg of the compounds admixed with a solid or liquid pharmaceutical carrier or diluent.

The compounds of formula I$a$ exhibit especially interesting activity, especially 6-methyl-8S-(3-pyridylamino)ergoline.

The compounds of formula I may be administered in pharmaceutically acceptable acid addition salt form. The present invention also provides a pharmaceutical composition comprising a compound of formula I, in free base form or in pharmaceutically acceptable acid addition salt form, in association with a pharmaceutical carrier or diluent.

Such compositions may be formulated in conventional manner, so as to be, for example, a solution or a tablet.

Further acids suitable for salt formation include methane sulphonic acid and malic acid.

We claim:

1. A compound of formula I:

wherein R is 3-pyridyl or 3-pyridyl mono- or di-substituted by lower alkyl having 1 to 4 carbon atoms, lower alkoxy having 1 to 4 carbon atoms, lower alkylthio having 1 to 4 carbon atoms, phenoxy, fluoro, chloro, bromo, hydroxy, or the group $$-N\begin{matrix}R_1\\R_2\end{matrix}$$

wherein each of $R_1$ and $R_2$ is, independently hydrogen or lower alkyl, having 1 to 4 carbon atoms,
or a pharmaceutically acceptable acid addition salt thereof.

2. A method of treating prolactin lactation in animals, which comprises administering to an animal in need of such treatment a therapeutically effective amount of a compound of claim 1.

3. A method of treating M. Parkinson in animals, which comprises administering to an animal in need of such treatment a therapeutically effective amount of a compound of claim 1.

4. A compound of claim 1 wherein the 3-pyridyl is substituted by methoxy, ethoxy, isopropoxy, n-butoxy, tert-butoxy or methylthio group.

5. The compound of claim 1 which is 6-methyl-8S-(3-pyridylamino)ergoline.

6. The compound of claim 1 which is 6-methyl-8R-(3-pyridylamino)ergoline.

7. The compound of claim 1 which is 6-methyl-8S-(2-methoxy-5-pyridylamino)ergoline.

8. The compound of claim 1 which is 6-methyl-8R-(2-methoxy-5-pyridylamino)ergoline.

9. The compound of claim 1 which is 6-methyl-8S-(2-ethoxy-5-pyridylamino)ergoline.

10. The compound of claim 1 which is 6-methyl-8R-(2-ethoxy-5-pyridylamino)ergoline.

11. The compound of claim 1 which is 6-methyl-8S-(2-isopropoxy-5-pyridylamino)ergoline.

12. The compound of claim 1 which is 6-methyl-8R-(2-isopropoxy-5-pyridylamino)ergoline.

13. The compound of claim 1 which is 6-methyl-8S-(2-n-butoxy-5-pyridylamino)ergoline.

14. The compound of claim 1 which is 6-methyl-8R-(2-n-butoxy-5-pyridylamino)ergoline.

15. The compound of claim 1 which is 6-methyl-8S-(2-tert.butoxy-5-pyridylamino)ergoline.

16. The compound of claim 1 which is 6-methyl-8R-(2-tert.butoxy-5-pyridylamino)ergoline.

17. The compound of claim 1 which is 6-methyl-8S-(2-phenoxy-5-pyridylamino)ergoline.

18. The compound of claim 1 which is 6-methyl-8R-(2-phenoxy-5-pyridylamino)ergoline.

19. The compound of claim 1 which is 6-methyl-8R-(2-methyl-5-pyridylamino)ergoline.

20. The compound of claim 1 which is 6-methyl-8S-(2-methyl-5-pyridylamino)ergoline.

21. The compound of claim 1 which is 6-methyl-8R-(2-hydroxy-5-pyridylamino)ergoline.

22. The compound of claim 1 which is 6-methyl-8S-(2-hydroxy-5-pyridylamino)ergoline.

23. The compound of claim 1 which is 6-methyl-8R-(2-chloro-5-pyridylamino)ergoline.

24. The compound of claim 1 which is 6-methyl-8S-(2-chloro-5-pyridylamino)ergoline.

25. The compound of claim 1 which is 6-methyl-8R-(2,6-dimethoxy-3-pyridylamino)ergoline.

26. The compound of claim 1 which is 6-methyl-8S-(2,6-dimethoxy-3-pyridylamino)ergoline.

27. The compound of claim 1 which is 6-methyl-8R-(2-dimethylamino-5-pyridylamino)ergoline.

28. The compound of claim 1 which is 6-methyl-8S-(2-dimethylamino-5-pyridylamino)ergoline.

29. The compound of claim 1 which is 6-methyl-8R-(2-amino-5-pyridylamino)ergoline.

30. The compound of claim 1 which is 6-methyl-8S-(2-amino-5-pyridylamino)ergoline.

31. The compound of claim 1 which is 6-methyl-8S-(2-thiomethyl-5-pyridylamino)ergoline.

32. The compound of claim 1 which is 6-methyl-8R-(2-thiomethyl-5-pyridylamino)ergoline.

33. A method according to claim 2, wherein the compound is administered at a daily dose of from about 0.005 milligrams to about 50 milligrams per kilogram of animal body weight.

34. A method according to claim 2, wherein the compound is administered at a daily dosage of from about 0.5 milligrams to about 50 milligrams.

35. A method according to claim 2, wherein the compound is administered in a unit dosage form comprising from about 0.1 milligrams to about 25 milligrams of said compound per unit dosage.

36. A method according to claim 2, in which the compound is 6-methyl-8S-(3-pyridylamino)ergoline.

37. A method according to claim 3, wherein the compound is administered at a daily dosage of from about 0.005 milligrams to about 50 milligrams per kilogram of animal body weight.

38. A method according to claim 3, wherein the compound is administered at a daily dosage of from about 0.5 milligrams to about 50 milligrams.

39. A method according to claim 3, wherein the compound is administered in a unit dosage from comprising from about 0.1 milligrams to about 25 milligrams of said compound per unit dosage.

40. A method according to claim 3, in which the compound is 6-methyl-8S-(3-pyridylamino)ergoline.

* * * * *